United States Patent [19]
McGarry et al.

[11] Patent Number: 6,036,710
[45] Date of Patent: Mar. 14, 2000

[54] APPARATUS FOR FORMATION OF A HOLE IN A BLOOD VESSEL

[75] Inventors: Richard A. McGarry, Norwalk; Hanspeter Robert Bayer, Meriden, both of Conn.

[73] Assignee: United States Surgical, Norwalk, Conn.

[21] Appl. No.: 08/933,892

[22] Filed: Sep. 19, 1997

Related U.S. Application Data

[63] Continuation-in-part of application No. 08/726,106, Oct. 4, 1996, abandoned.

[51] Int. Cl.[7] .................................................. A61B 17/32
[52] U.S. Cl. ............................................................ 606/184
[58] Field of Search ............................... 606/1, 159, 170, 606/171, 180, 184; 604/22; 30/240, 263

[56] References Cited

U.S. PATENT DOCUMENTS

| | | |
|---|---|---|
| D. 281,721 | 12/1985 | Scanlan . |
| D. 372,310 | 7/1996 | Hartnett . |
| 3,776,237 | 12/1973 | Hill et al. . |
| 4,018,228 | 4/1977 | Goosen ..................................... 606/184 |
| 4,122,855 | 10/1978 | Tezel . |
| 4,216,776 | 8/1980 | Downie et al. . |
| 4,243,048 | 1/1981 | Griffin . |
| 4,388,925 | 6/1983 | Burns . |
| 4,469,109 | 9/1984 | Mehl . |
| 4,699,154 | 10/1987 | Lindgren . |
| 4,733,671 | 3/1988 | Mehl . |
| 4,738,261 | 4/1988 | Enstrom . |
| 4,785,826 | 11/1988 | Ward . |
| 4,832,045 | 5/1989 | Goldberger . |
| 5,005,585 | 4/1991 | Mazza . |
| 5,129,913 | 7/1992 | Ruppert ..................................... 606/184 |
| 5,139,508 | 8/1992 | Kantrowitz et al. . |
| 5,172,702 | 12/1992 | Leigh et al. . |
| 5,183,053 | 2/1993 | Yeh et al. . |
| 5,186,178 | 2/1993 | Yeh et al. . |
| 5,192,294 | 3/1993 | Blake, III ................................. 606/184 |
| 5,304,193 | 4/1994 | Zhadanov . |
| 5,423,330 | 6/1995 | Lee . |
| 5,515,861 | 5/1996 | Smith . |

*Primary Examiner*—Michael Buiz
*Assistant Examiner*—William W. Lewis

[57] ABSTRACT

An apparatus for forming a non-circular opening in tissue includes an elongate body having a first tissue engaging edge associated with a distal end portion thereof, a punch head disposed adjacent the distal end portion of the elongate body, and defining a second tissue engaging edge associated therewith. The first and second tissue engaging edges each define a general racetrack configuration characterized by first and second opposed straight edge portions interconnected by generally arcuate edge portions. At least one of the first and second tissue engaging edges is adapted to cut tissue. The elongate body and the punch head are adapted for relative movement such that the first and second tissue engaging edges cooperate to cut tissue disposed therebetween to thereby form a general racetrack-shaped opening in tissue.

29 Claims, 16 Drawing Sheets

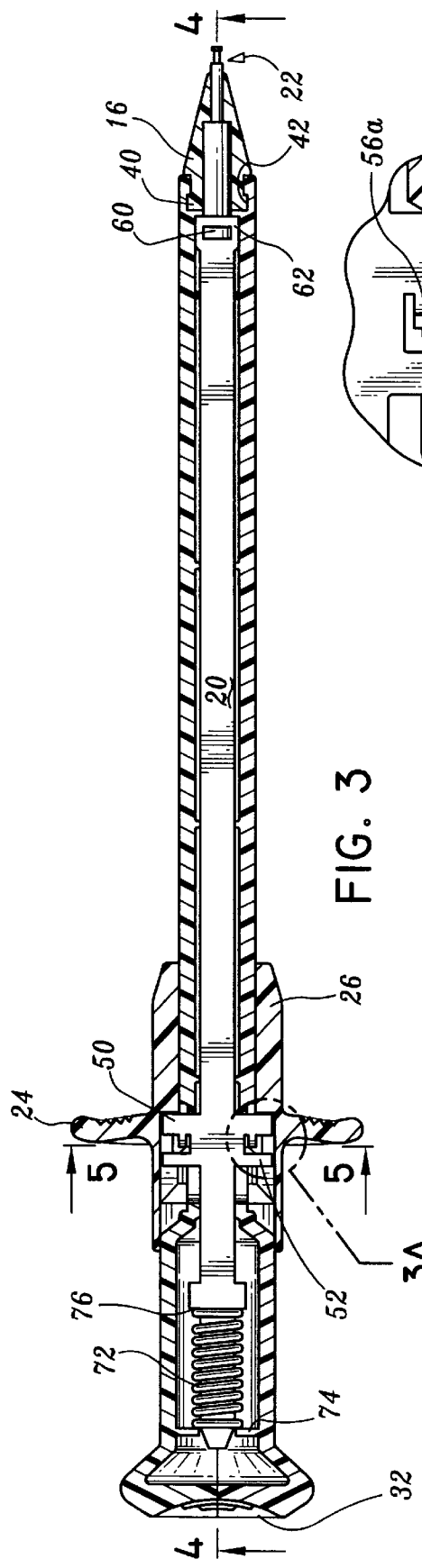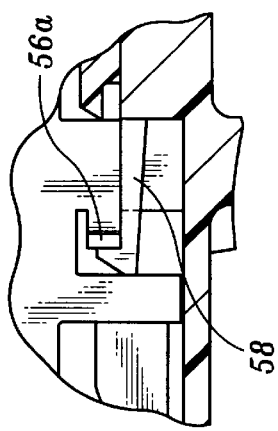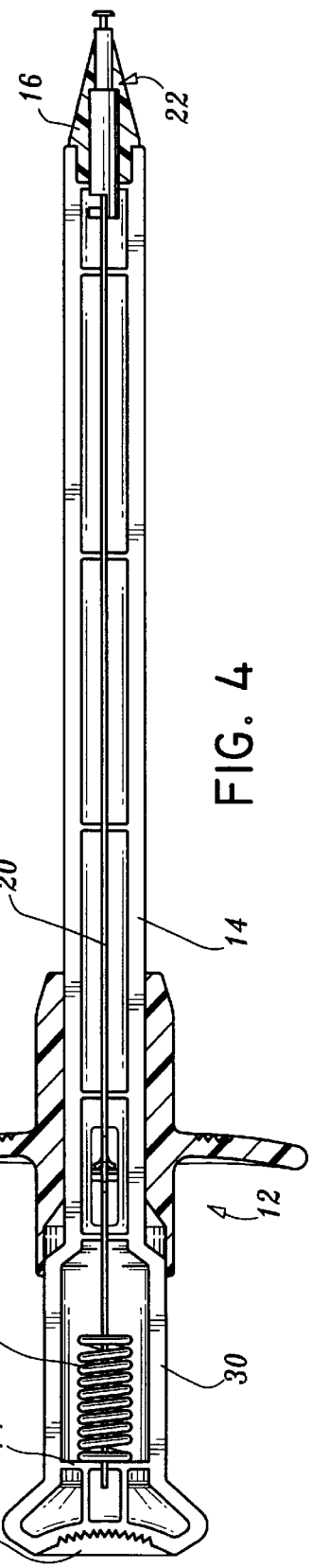
FIG. 3
FIG. 3A
FIG. 4

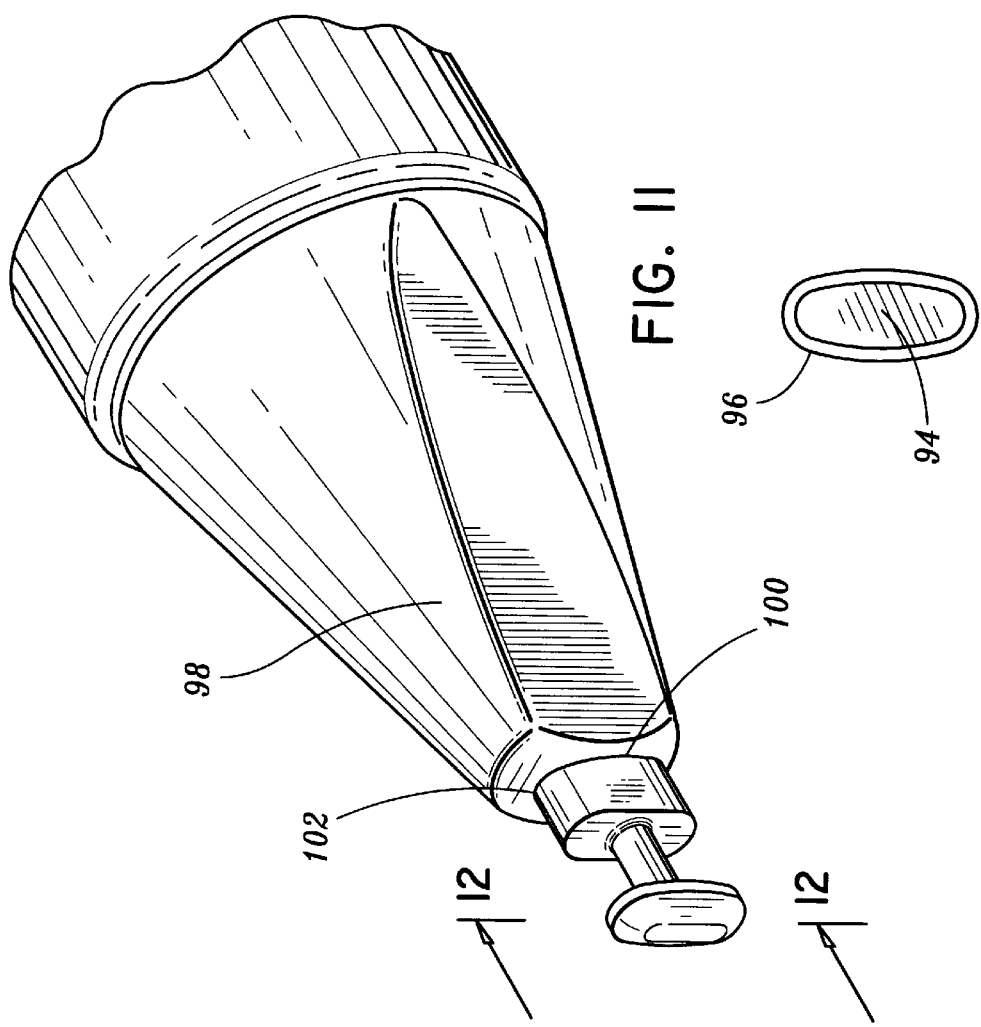
FIG. 11
FIG. 12
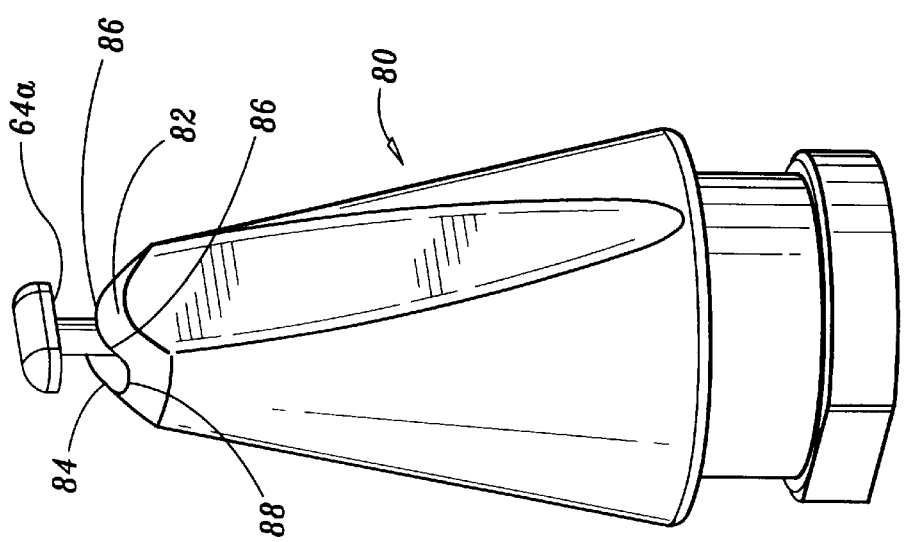
FIG. 10

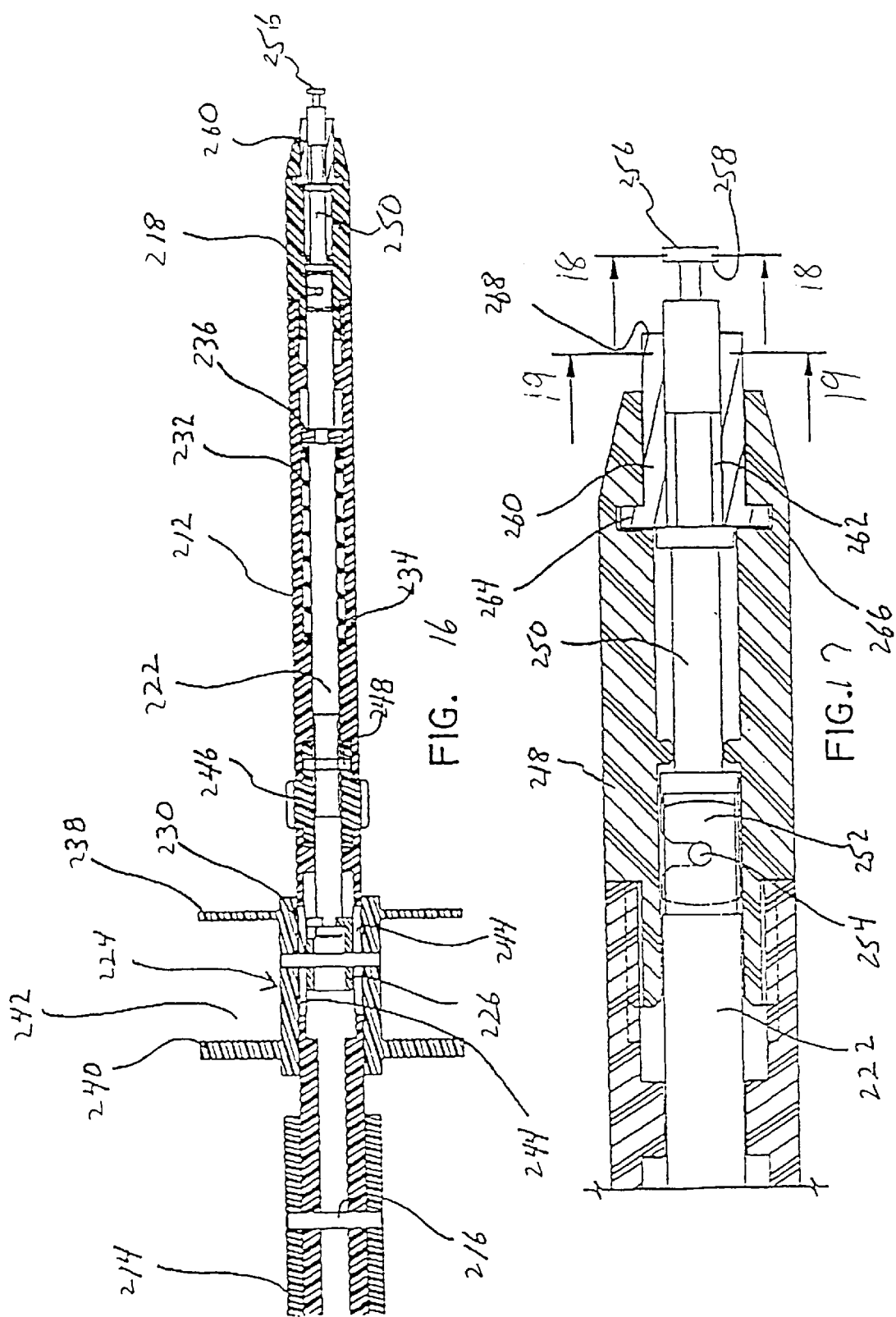

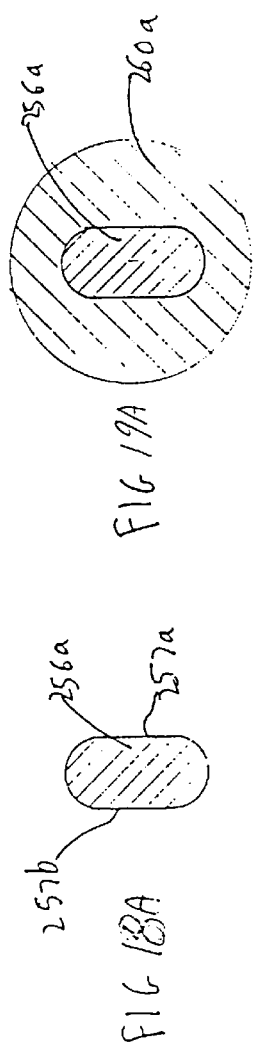
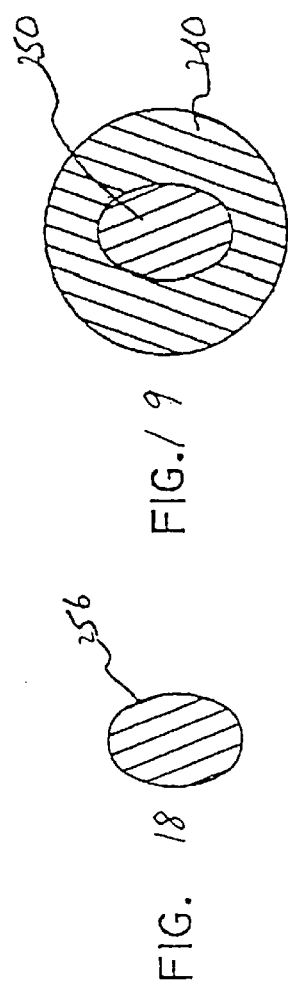
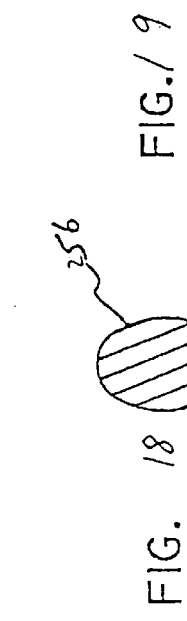
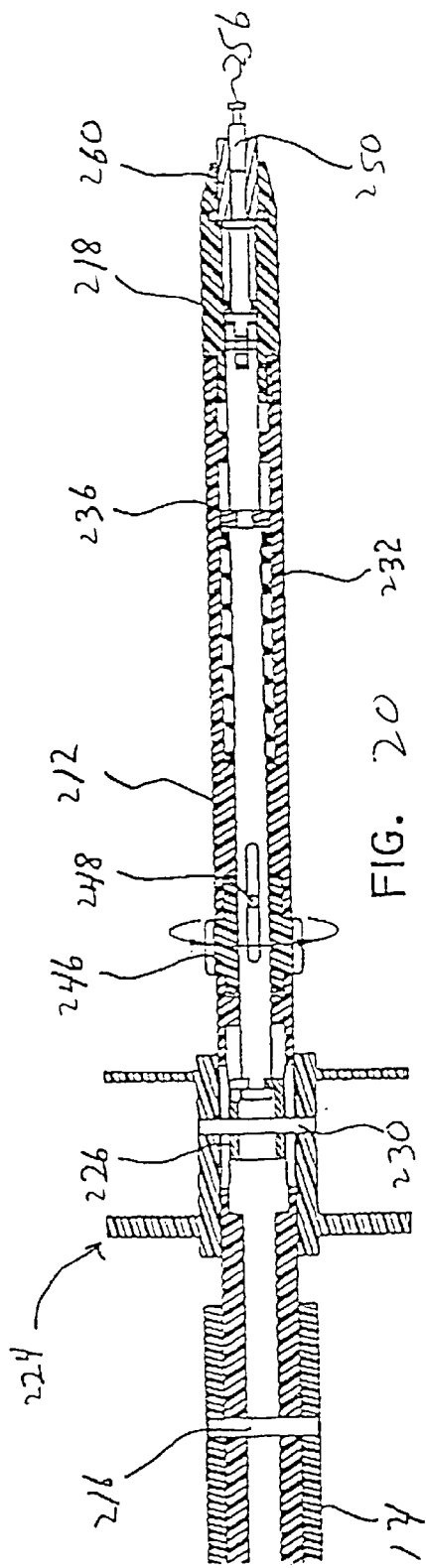

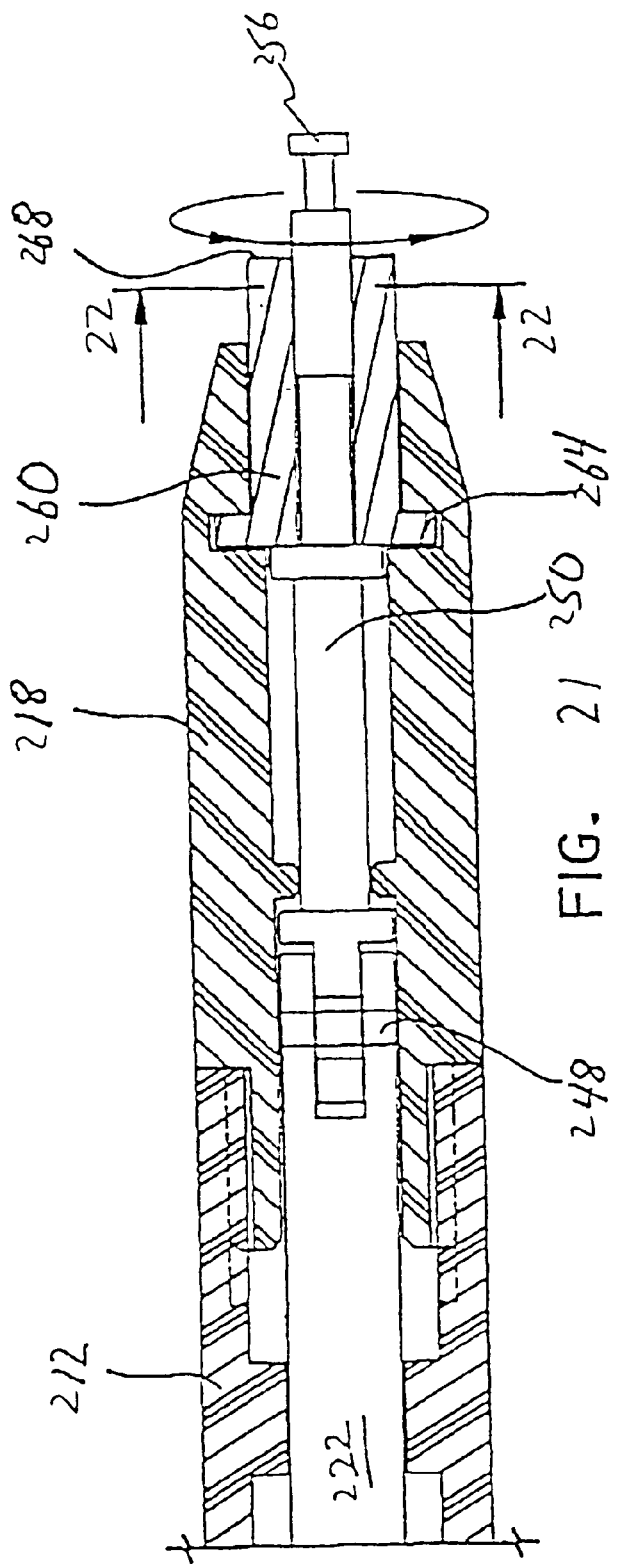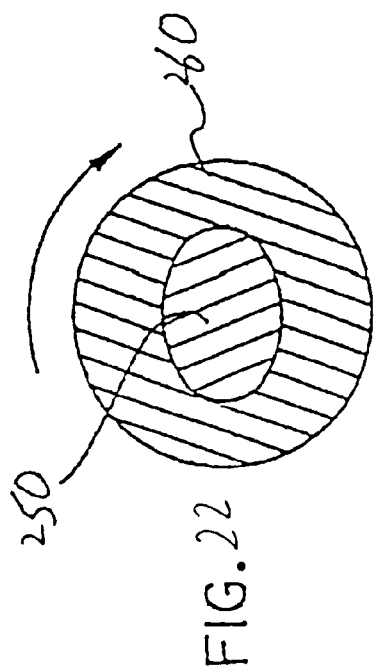
FIG. 21
FIG. 22

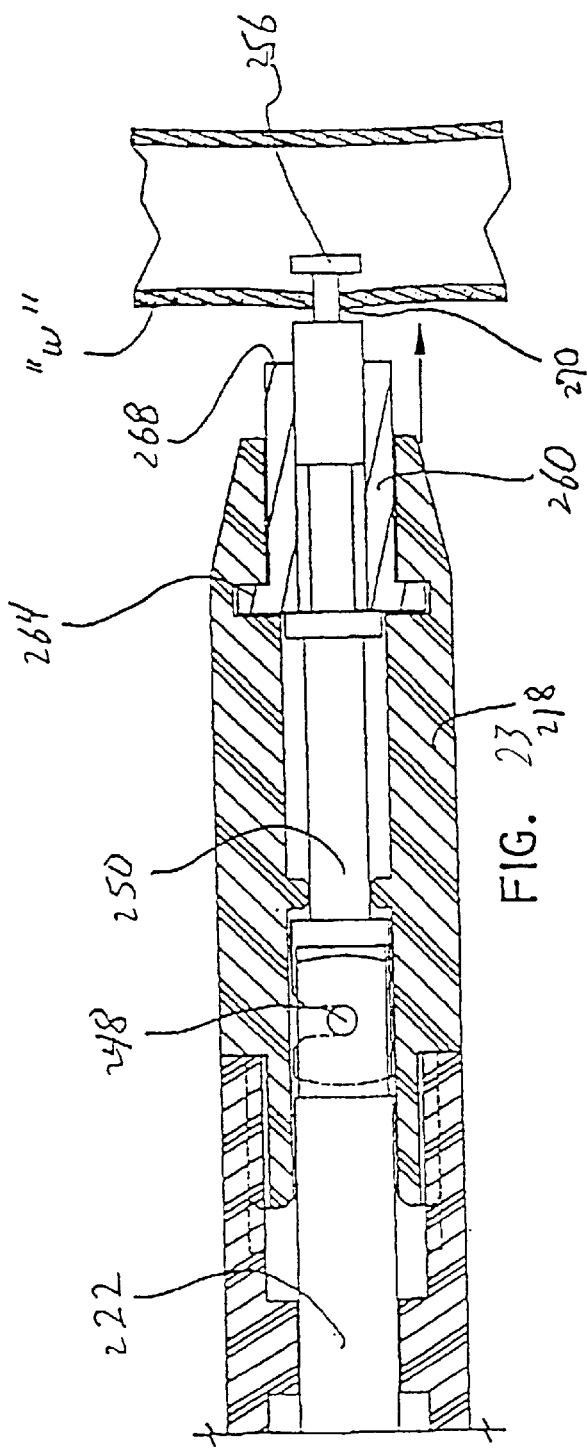
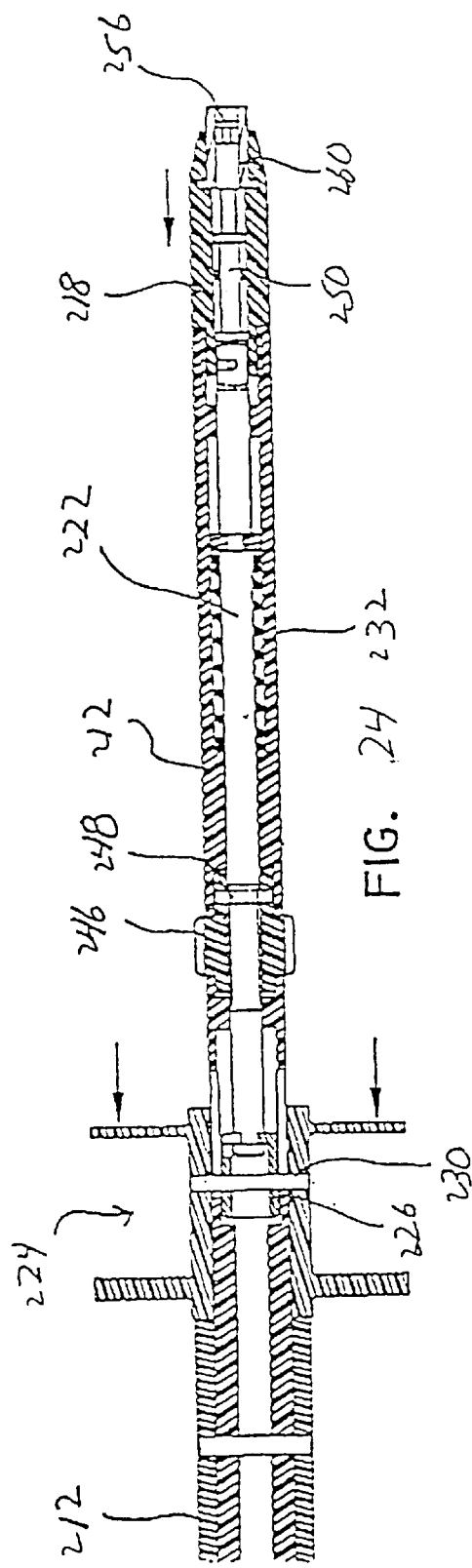

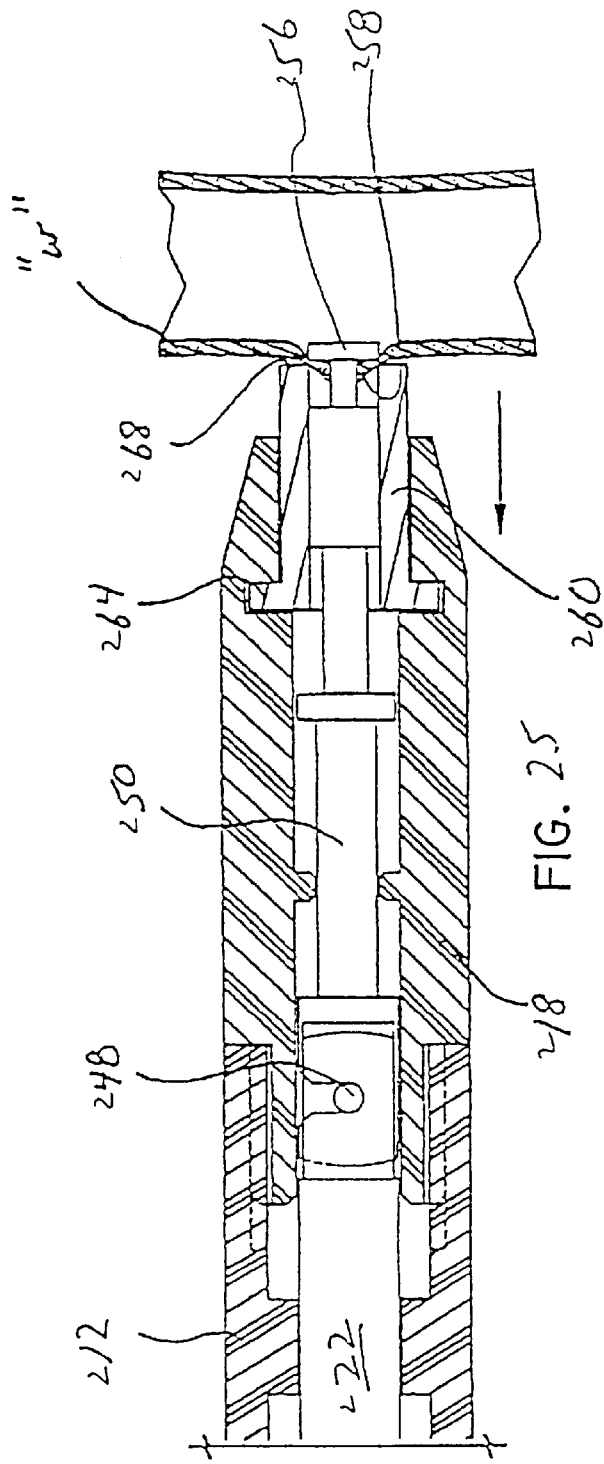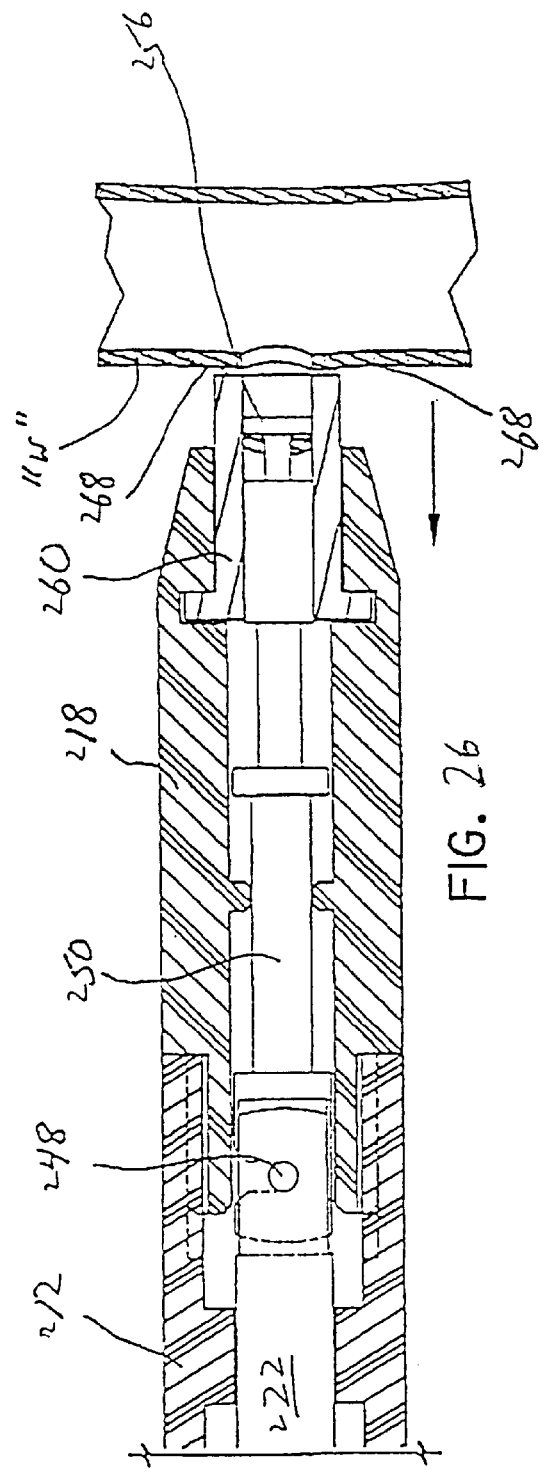

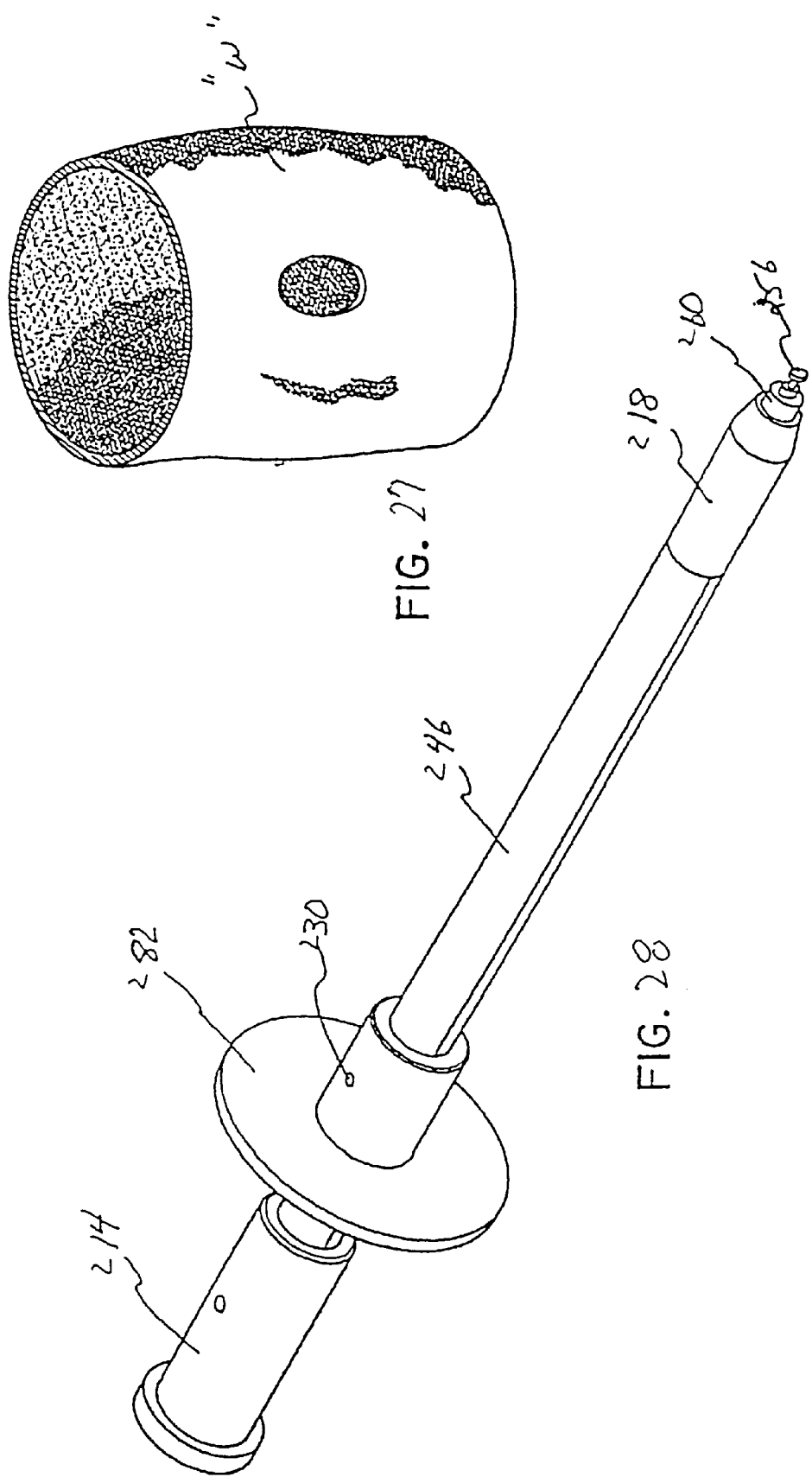

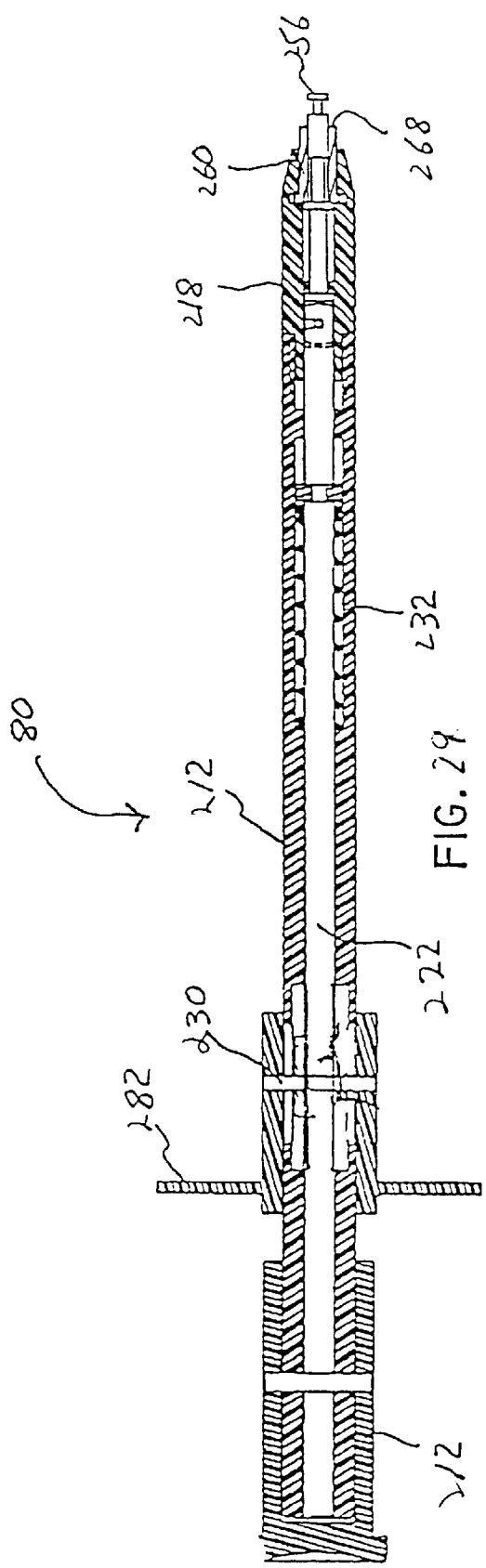
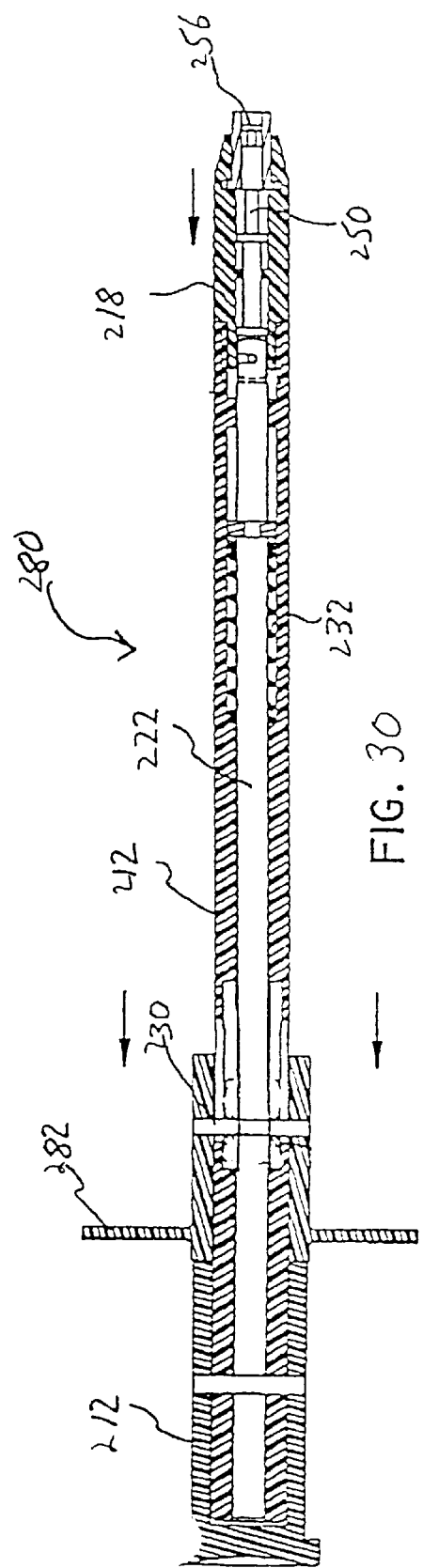

APPARATUS FOR FORMATION OF A HOLE IN A BLOOD VESSEL

CROSS-REFERENCE TO RELATED APPLICATIONS

This is a continuation-in-part of application Ser. No. 08/726,106 filed Oct. 4, 1996, now abandoned.

BACKGROUND

1. Technical Field

The present disclosure relates generally to surgical instruments and, more particularly, to a surgical instrument for forming a hole in a blood vessel wall.

2. Background of Related Art

In cardiac surgery, it is often necessary to connect a prepared vein to a coronary artery to bypass a diseased area or areas of the artery. Typically, the prepared vein is attached about an opening formed in, for example, the ascending aorta, and then anastomosed to the aorta. In the past, the opening had been formed with the use of a scalpel instrument or scissor instrument. However, aortic punch instruments or perforators have been utilized to create the opening in the vessel wall.

U.S. Pat. No. 4,018,228 to Goosen discloses a surgical punch apparatus including an elongate hollow sleeve and an elongated rod extending through one end of the sleeve and reciprocally moveable therein. The elongated rod has a distal narrowed end portion including a fixed cylindrical blade while the hollow sleeve has a hollow cylindrical blade removably attached thereto. The elongated rod is activated by a handle which pulls the rod and blade into the hollow sleeve thereby forming an opening in the vessel tissue disposed therebetween.

U.S. Pat. No. 4,216,776 to Downie et al. discloses a similar device including an elongated stem and a coaxial disc having an exterior circumferential disc surface separated from the rest of the stem. An elongated tube is mounted on the stem and is slidable thereon to telescope over the coaxial disc. The elongated tube and exterior disc are devoid of sharp cutting edges, but, are dimensioned such that an annular clearance is defined therebetween. The effect of this clearance is that the tissue disposed between the tube and disc is separated by a tensional force instead of cutting or shearing of the tissue.

While the above-devices described in the Goosen '228 patent and the Downie '776 patent are well known, it is desirous to provide an apparatus with improved characteristics and which can provide, through a clean shearing action, a non-circular, preferably, generally racetrack-shaped opening in the blood vessel wall. A racetrack-shaped opening is particularly advantageous when using an anastomosis instrument during for example, a coronary artery bypass grafting (CABG) procedure. In particular, it has been found that the racetrack configuration assists in everting of the blood vessel to appropriately position the vessel wall portions adjacent the opening with respect to the apparatus for firing of the anastomosis clips or staples. In addition, since the vein graft is typically attached to the aorta at an angle less than 90 degrees, e.g., 45 degrees, because the end of the graft is cut at an angle, the racetrack configuration more closely conforms to the shape of the cut end.

SUMMARY

Accordingly, the present disclosure is directed to an apparatus for forming a non-circular opening in tissue. The apparatus includes an elongate body having a first tissue engaging edge associated with a distal end portion thereof and a punch head disposed adjacent the distal end portion of the elongate body, and defining a second tissue engaging edge associated therewith. The first and second tissue engaging edges each define a general racetrack configuration characterized by first and second opposed straight edge portions interconnected by generally arcuate edge portions. At least one of the first and second tissue engaging edges is adapted to cut tissue. The elongate body and the punch head are adapted for relative movement such that the first and second tissue engaging edges cooperate to cut tissue disposed therebetween to thereby form a general racetrack-shaped opening in tissue. Preferably, the first and second tissue engaging edges are each adapted to cut tissue.

In another preferred embodiment, an apparatus for forming a non-circular opening in the wall of a blood vessel, includes a housing, an elongate body mounted with respect to the housing and having proximal and distal end portions, a cutting element associated with a distal end portion of the elongate body and having a peripheral cutting edge defining a longitudinal opening in the cutting element whereby the peripheral cutting edge defines a general racetrack configuration having opposed straight edge portions connected by arcuate edge portions, and a punch element disposed adjacent the distal end portion of the elongate body and operatively connected to the housing, and having a punch head dimensioned to support tissue. At least one of the elongate body and the housing is movable relative to the other between an unactuated position wherein the peripheral cutting edge of the cutting element and the punch heed of the punch element are displaced and an actuated position wherein the peripheral cutting edge and the punch head are approximated to cooperate to cut tissue supported by the punch head.

In one embodiment, the peripheral cutting edge of the cutting element includes opposed straight edge portions connected by arcuate edge portions. Alternatively, the cutting element may define a general dome-shaped distal element to thereby define a sloped peripheral cutting edge. The punch head may define a cross-sectional dimension approximating an internal dimension of the longitudinal opening of the cutting element such that in the actuated position the punch head is at least partially received within the longitudinal opening. Preferably, the punch head defines a peripheral cutting edge adapted to cooperate with the peripheral cutting edge of the cutting element to cut tissue. The peripheral cutting edge of the punch head may define a general racetrack configuration having opposed straight edge portions connected by arcuate edge portions.

A method for forming an opening in a blood vessel wall is also disclosed.

BRIEF DESCRIPTION OF THE DRAWINGS

Various preferred embodiments are described herein with reference to the drawings, wherein:

FIG. 1A is an enlarged view of the distal end portion of the apparatus illustrating the racetrack configuration of the vessel cutting structure;

FIG. 3 is a side cross-sectional view of the apparatus in an unactuated position;

FIG. 3A is an enlarged isolated view of FIG. 3 illustrating the mechanism for mounting the housing to the elongate member;

FIG. 4 is a cross-sectional view of the apparatus taken along the lines 4—4 of FIG. 3;

FIG. 10 is an alternate embodiment illustrating a dome-shaped cutting element;

FIG. 11 is another alternate embodiment illustrating an oblate configuration of the punch structure; and FIG. 12 is a view taken along lines 12—12 of FIG. 11 further illustrating the oblate configuration of the punch head.

FIG. 16 is a cross-sectional view of the apparatus taken along the lines 16—16 of FIG. 15;

FIG. 17 is an enlarged cross-sectional view of the distal end of the apparatus;

FIG. 18 is a cross-sectional view of the apparatus taken along the line 18—18 of FIG. 17 illustrating the elliptical configuration of the distal cutting head of the punch rod;

FIG. 18A is a cross-sectional view of the alternate embodiment of the distal cutting head of the punch rod;

FIG. 19 is a cross-sectional view of the apparatus taken along the line 19—19 of FIG. 17 illustrating the elliptical configuration of the cutting collar;

FIG. 19A is a cross-sectional view of an alternate embodiment of the cutting collar;

FIG. 20 is a view similar to the view of FIG. 17 illustrating rotation of the manually operable member and corresponding movement of the punch rod and cutting collar;

FIG. 21 is an enlarged view of the distal end of the apparatus further illustrating the rotational movement of the punch rod and the cutting collar;

FIG. 22 is a cross-sectional view taken along the line 22—22 of FIG. 21;

FIG. 23 is an enlarged cross-sectional view of the distal end of the apparatus illustrating positioning of the artery wall within the recessed portion of the punch rod in accordance with a preferred method of use of the apparatus;

FIG. 24 is a cross-sectional view similar to the view of FIG. 16 illustrating proximal movement of the actuating member and corresponding movement of the punch rod to cut an opening in the artery wall;

FIGS. 25–26 are enlarged cross-sectional views of the distal end of the apparatus illustrating the sequence of motion of the punch rod upon proximal movement of the actuating member;

FIG. 27 is a view illustrating the elliptical opening formed in the artery wall;

FIG. 28 is a perspective view of an alternative embodiment of the apparatus of FIG. 13 incorporating a disc-shaped handle;

FIG. 29 is a cross-sectional view of the apparatus of FIG. 28 illustrating the actuating member and punch rod in the unactuated position; and FIG. 30 is a cross-sectional view of the apparatus of FIG. 28 illustrating the actuating member and punch rod in the actuated position.

DETAILED DESCRIPTION OF THE PREFERRED EMBODIMENTS

Figure 1:
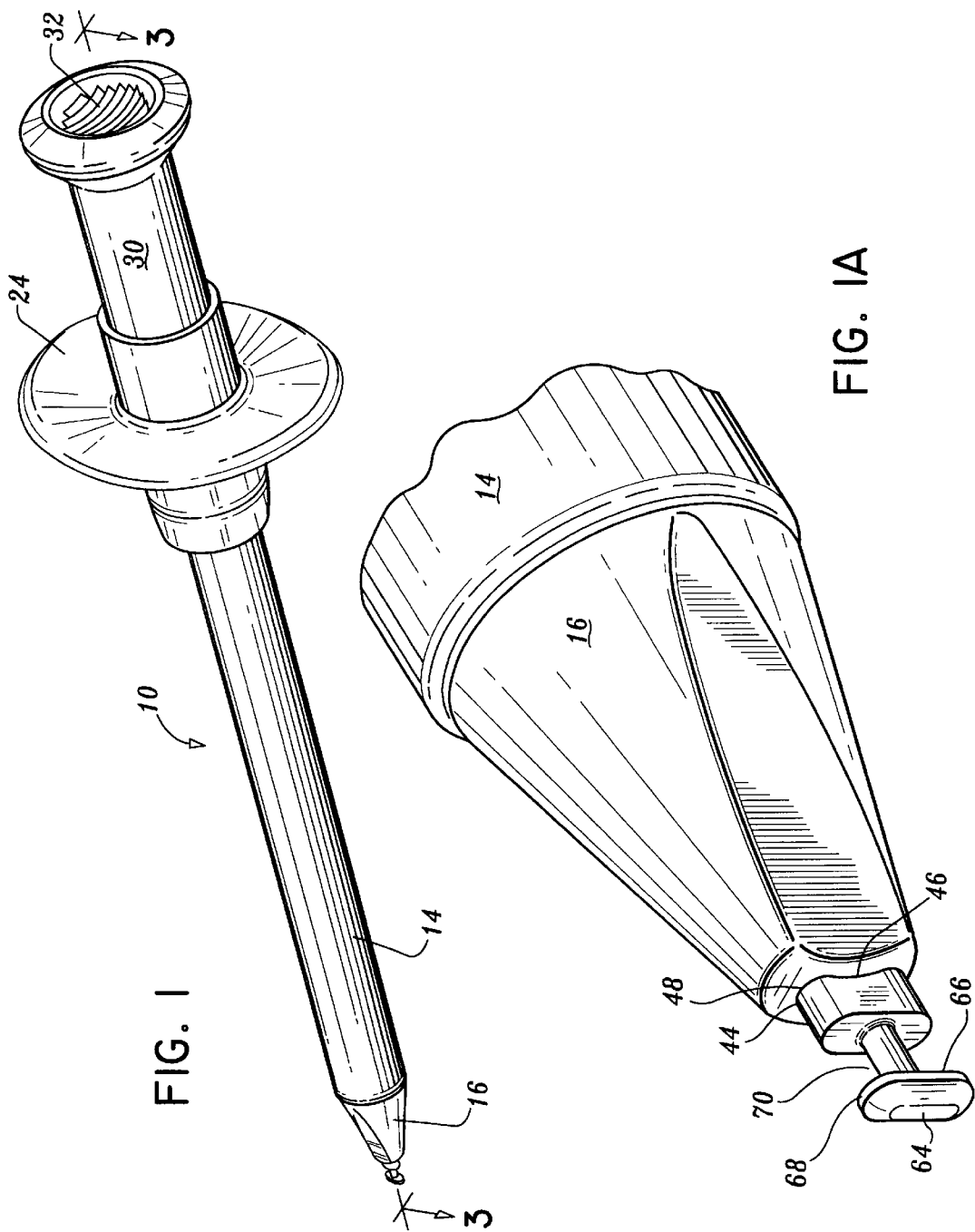
FIG. 1 is a perspective view the apparatus for forming an opening in a wall of a blood vessel in accordance with the principles of the present disclosure.

In general, the objective of the apparatus is to form an opening in the wall of a blood vessel to facilitate a vein grafting procedure.

In the drawings and in the description which follows, the term "proximal", as is traditional, will refer to the end of the apparatus which is closest to the operator, while the term "distal" will refer to the end of the apparatus which is furthest from the operator.

Referring now to the drawings wherein like reference numerals identify similar structural elements herein, FIG. 1 illustrates in perspective view the apparatus constructed in accordance with a preferred embodiment of the present disclosure and designated generally by reference numeral 10. Surgical apparatus 10 is particularly contemplated for facilitating the formation of a non-circular hole, in particular, a general racetrack-shaped opening, in a coronary artery (e.g., the left anterior descending (LAD) coronary artery, right coronary artery, aorta) during a coronary artery bypass grafting (CABG) procedure.

Figure 2:
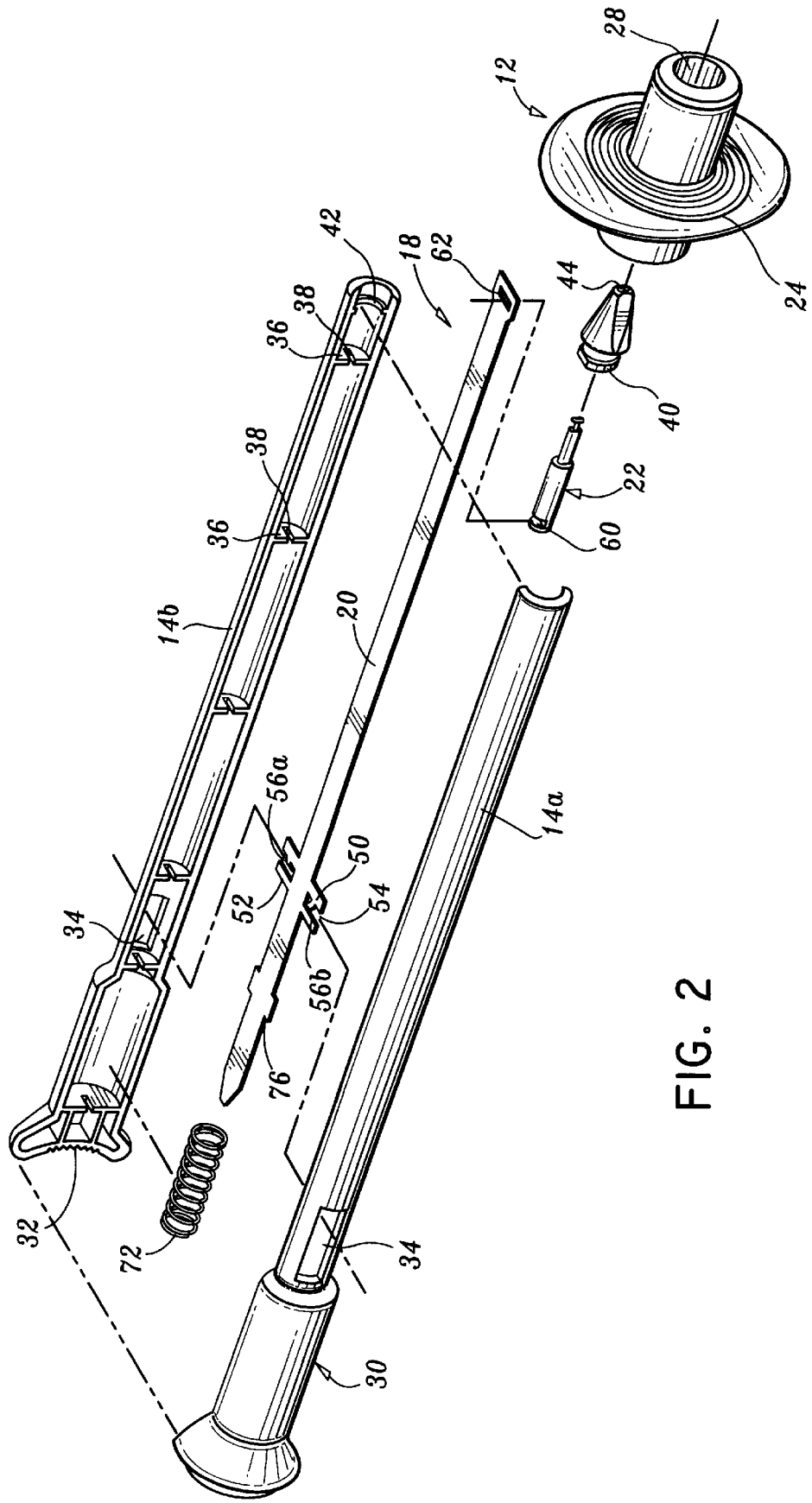
FIG. 2 is a perspective view of the apparatus with parts separated illustrating the housing, elongate body and punch structure disposed within the elongate body.

Referring now to FIGS. 1–3, apparatus 10 includes housing or handle 12, elongate body 14 mounted with respect to the housing 12, cutting collar or element 16 mounted to the distal end of the elongate body 14 and punch head structure 18 consisting of elongate plate 20 and punch head 22 connected to the distal end of the plate 20. Housing 12 includes a disc-shaped grasping portion 24 dimensioned for grasping engagement by the user and tubular portion 26. Tubular portion 26 defines a longitudinal opening 28.

Elongate body 14 consists of body half sections 14a, 14b connected to each other along their peripheral areas by adhesives, screws or the like. Elongate body 14 is preferably fabricated from a suitable material such as stainless steel, aluminum or a rigid polymeric material, e.g., polycarbonate. Elongate body 14 has actuating portion 30 at its proximal end. Actuating portion 30 may be integrally formed with elongate body 14 as shown or may be a separate component connected to the elongate body 14 by conventional means. Actuating portion 30 includes thumb recess 32 dimensioned to accommodate the user's thumb during operation of the apparatus. Thumb recess 32 may include a roughened surface in the form of ribs to facilitate gripping engagement thereof.

Elongate body 14 further includes diametrically opposed window(s) or openings 34 formed in the outer wall of half sections 14a, 14b adjacent actuating portion 30 and a plurality (e.g., 4) of mounting projections 36 defined within the interior of each half section. Mounting projections 36 define slots 38 therein which serve in mounting elongate plate 20 within the elongate body 14.

With continued reference to FIGS. 1–4, cutting collar 16 is mounted to the distal end of elongate body 14 by reception of annular rib 40 of the cutting collar 16 within a correspondingly dimensioned recess 42 (FIG. 2) defined in the elongate body 14. Cutting collar 16 includes tissue engaging edge 44 at its remote distal end (FIG. 1A). Tissue engaging or cutting edge 44 has a general racetrack configuration which defines a generally racetrack-shaped opening at the distal end of the cutting collar 16. The racetrack configuration of tissue engaging edge 44 is characterized by opposed generally straight edge portions 46 which are connected by opposed arcuate edge portions 48. The racetrack configuration provides advantages in vessel closure as will be appreciated from the description provided hereinbelow. Preferably, tissue engaging edge 44 is a sharp cutting edge, but, it is also envisioned that the engaging edge 44 may be blunt.

Figure 5:
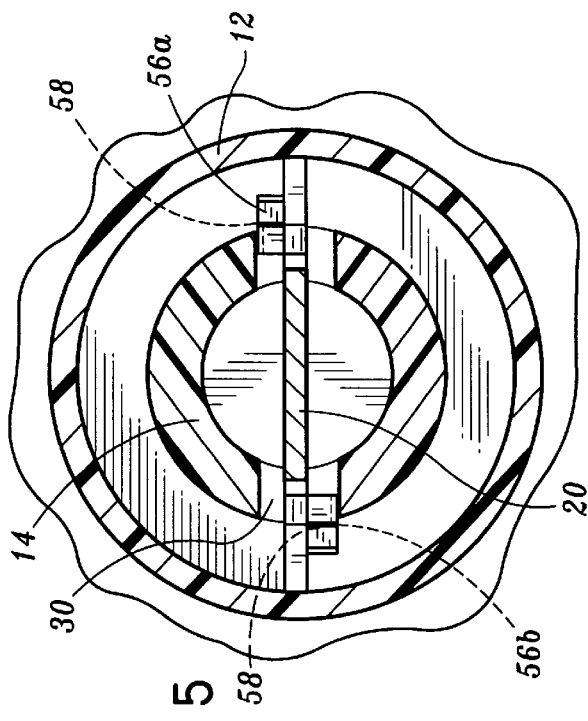
FIG. 5 is a cross-sectional view taken along the lines 5—5 of FIG. 3 further illustrating the mechanism for mounting the housing to the elongate member.

Elongate plate 20 of punch head structure 18 is generally flat or planar so as to be received within slots 38 of projections 36 of the elongate body 14 in sliding relation therewith. Elongate plate 20 includes mounting structure in the form of first and second radial legs 50, 52 extending from each side of the elongate plate 20 and separated by gap 54. First and second radial legs 50, 52 extend through windows 34 of elongate body 14 into engagement with the interior of housing 12. First legs 50 each include locking detents 56a, 56b which extend in a general axial direction within gap 54. With particular reference to FIGS. 3A and 5, locking detents 56a, 56b extend in different directions relative to punch rod 20 as shown, i.e., locking detent 56a extends upwardly and locking detent 56b extends downwardly. Locking detents 56a, 56b are strategically dimensioned to lockingly engage corresponding locking hooks 58 (FIG. 3A) defined within the interior of housing 12 to connect the elongate plate 20 to the housing 12. Other means for fixedly mounting plate 20 to housing 12 are also envisioned including the use of adhesives, bayonet coupling, tongue and groove arrangements, etc.

With reference now to FIGS. 2–3, punch head 22 is mounted to the distal end of elongate plate 20 by corresponding reception of mounting leg 60 of the punch head 22 within rectangular aperture 62 defined at the distal end of elongate punch rod 20. Punch head 22 defines head portion 64 at its distal end as best shown in FIG. 1A. Head portion 64 is dimensioned to support tissue thereagainst during operation of the apparatus 10. Head portion 64 also has a peripheral edge 64a defining a racetrack configuration which approximates the racetrack configuration of tissue engaging edge 44 of cutting collar 16. More particularly, head portion 64 is characterized by diametrically opposed straight cutting edge portions 66 interconnected by diametrically opposed arcuate cutting edge portions 68. The cross-sectional dimension of head portion 64 generally approximates the internal dimension of the opening of cutting collar 16 such that the head portion 64 is at least partially received within the cutting collar 16 upon actuation of the apparatus. Punch head 22 further defines a recessed portion 70 adjacent head portion 64. Recessed portion 70 assists in retaining the vessel wall portion in a desired position relative to head portion 64 and cutting collar 16.

Apparatus 10 further includes coil spring 72 mounted about the proximal end of the elongate plate 20. Coil spring 72 engages bearing surface 74 of actuating portion 30 at its proximal end and transverse surface 76 of elongate plate 20 at its distal end to normally bias the actuating portion 30 and elongate body 14 to its proximalmost position, i.e., inactuated position, depicted in FIGS. 3 and 4.

Figure 6:
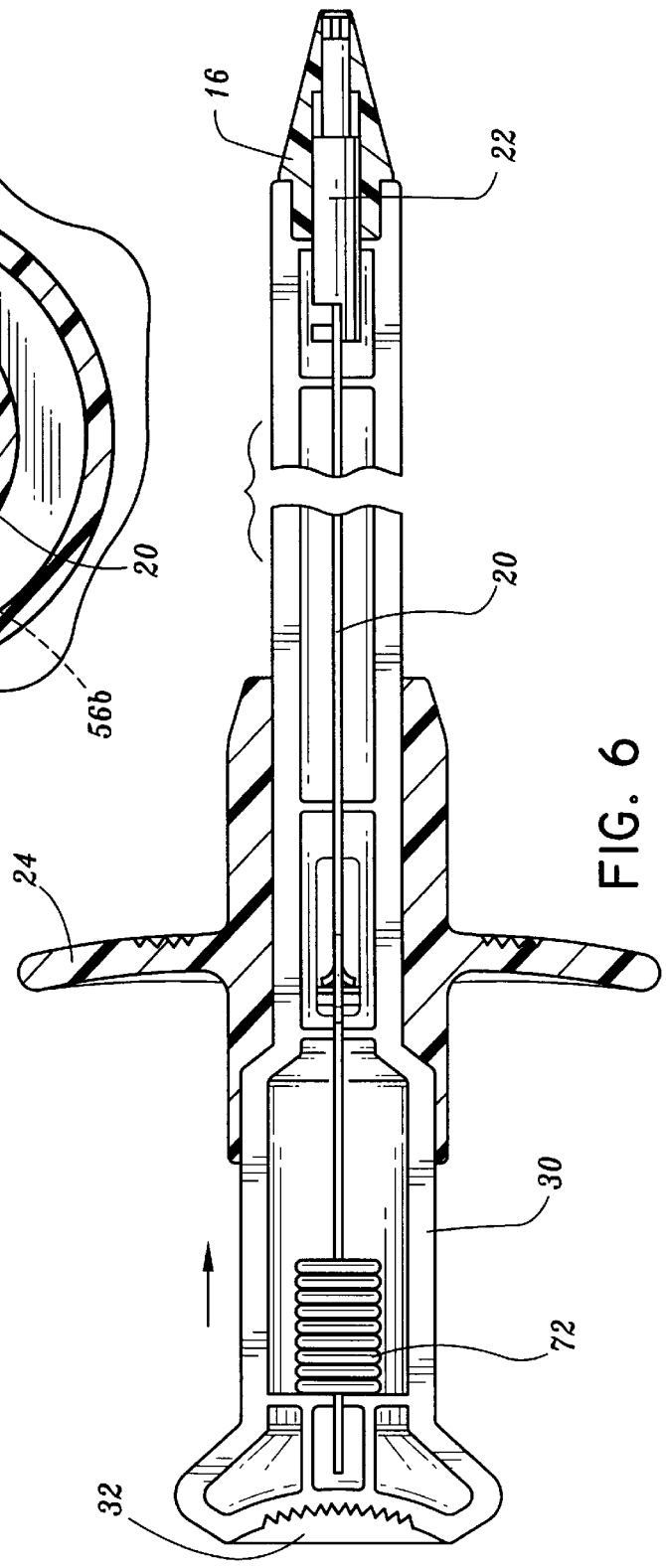
FIG. 6 is a cross-sectional view similar to the view of FIG. 4 illustrating actuation of the apparatus.
Figure 7:
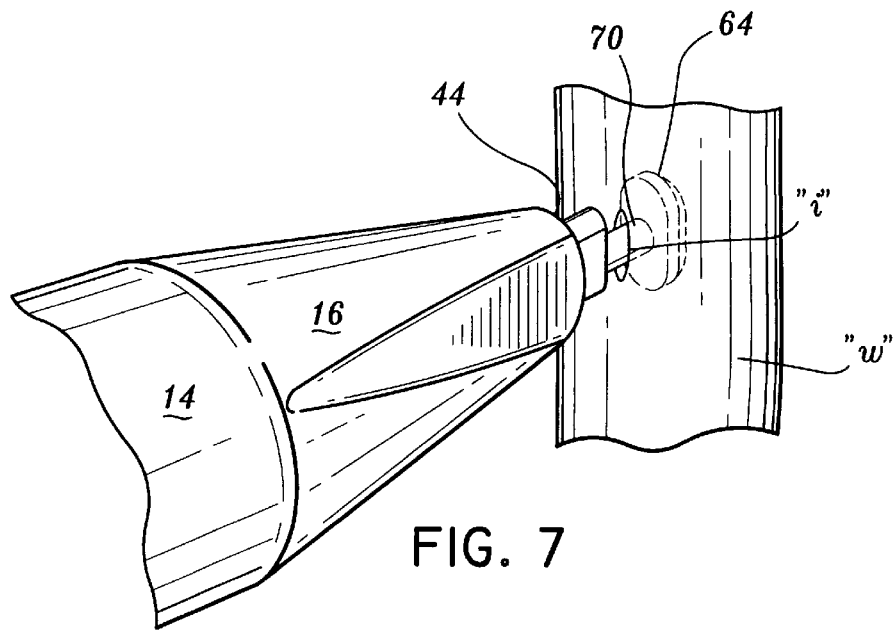
FIGS. 7–9 are views illustrating use of the apparatus to form the racetrack-shaped opening in the blood vessel wall.
Figure 8:
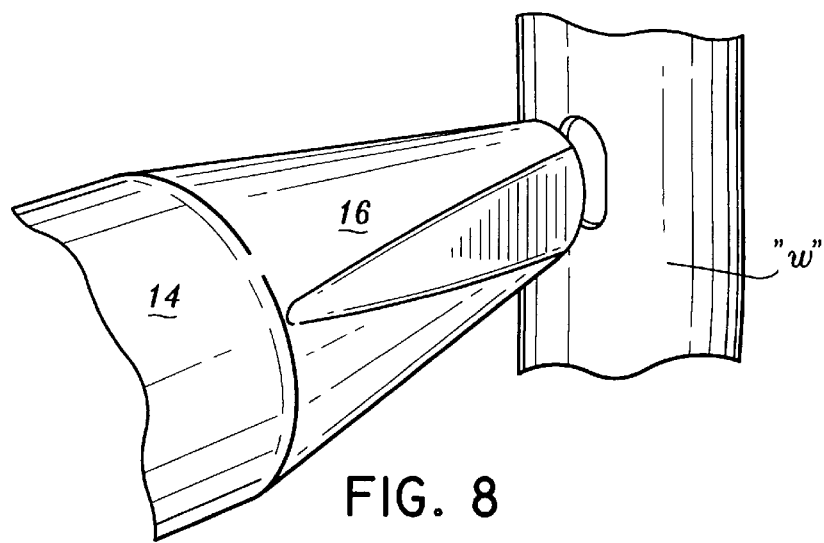
Figure 9:
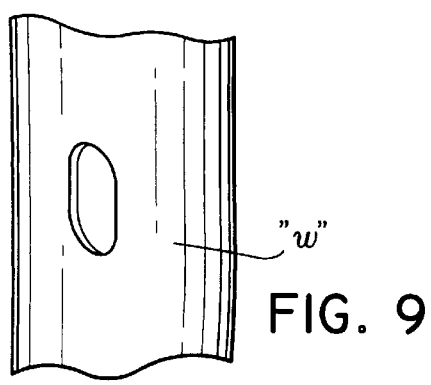

Referring now to FIGS. 4, 6 and 7–9, the use of the apparatus 10 in conjunction with forming a non-circular, i.e., racetrack shaped opening in the wall of a blood vessel, e.g., the aorta, for grafting of a vein during cardiac surgery will be discussed. FIG. 4 illustrates the apparatus in an unactuated position. FIG. 6 illustrates the apparatus in the actuated position. As depicted in FIG. 7, head portion 64 of punch head 22 is initially inserted through an incision "i" provided in the aorta wall "w". Preferably, the wall portion is accommodated within arcuate recessed portion 70 of punch head 22. It is to be appreciated that recessed portion 70 assists in retaining the vessel wall portion in a desired position relative to head portion 64 and cutting collar 16. The vessel wall "w" is interposed between tissue engaging edge 44 of cutting collar 16 and cutting edges 66, 68 of the head portion 64. Once the cutting surfaces are properly oriented, disc-shaped handle 24 is grasped with the index and middle finger of the user and actuating portion 30 is grasped with the user's thumb. Actuating member 30 is moved distally to move elongate body 14 and cutting collar 16 distally as indicated in FIG. 6 against the bias of spring 72. During movement of elongate body 14, handle 12, plate 20 and punch head 22 remain stationary. Elongate body 14 is able to move relative to plate 20 through the slotted arrangement of slots 38 of mounting projections 36 and plate element 20, i.e, the mounting projections 36 slide over the plate 20. In addition, the windows 34 (FIG. 2) in elongate body 14 permit the elongate body to move relative to radial legs 50, 52 of plate 20. Further distal movement of elongate body 14 and cutting collar 16 causes a shearing action on the blood vessel wall "w" between the cutting edge 44 of the cutting collar 16 and the cutting edges 64a of the punch head 22 to form the racetrack opening depicted in FIG. 9. In an alternate method of use of apparatus 10, actuating member 30 may remain stationary and disc-shaped grasping portion 24 of housing 12 may be pulled via the middle and index fingers proximally to cause retracting motion of punch head 22 to thereby effect a cutting of the vessel wall portion "w". It is also envisioned that in another alternate method of use, the cutting action may be effectuated through a combination of retracting motion of housing 12 and advancing motion of actuating member 30.

Upon actuation of the apparatus, grafting of a vessel is then performed, preferably, with an anastomosis instrument. One example of an anastomosis instrument that can be utilized to graft a vessel is disclosed in pending application Ser. No. 08/685,385, filed Jul. 23, 1996, the contents of which are incorporated herein by reference.

As indicated above, the racetrack-shaped hole formed in the blood vessel wall by the apparatus of the present disclosure provides several advantages. In particular, such configuration is particularly useful when using an anastomosis instrument during the grafting procedure. Moreover, the racetrack configuration assists in everting of the blood vessel to appropriately position the vessel walls portions adjacent the opening with respect to the apparatus for firing of the anastomosis clips or staples. In addition, since the vein graft is typically attached to the aorta at an angle less than 90, e.g. 45, the racetrack configuration more closely conforms to the shape of the cut end. In addition, the circular handle portion 24 permits the operator to rotate the instrument to a desired angular orientation.

FIG. 10 illustrates an alternate embodiment of the cutting collar of the instrument. In accordance with this embodiment, the cutting collar 80 incorporate a dome-shaped or conical distal cutting face 82 defining a dome-shaped or peripheral curved cutting edge 84 including sloped edges 86 connected by arcuate edges 88. The peripheral curved cutting edge 84 provides several advantages including the following: 1) the curved cutting edge 84 and the peripheral cutting edge 64a of head portion 64 of punch head 22 creates a scissoring action as the instrument is fired; 2) it reduces instantaneous cutting force; and 3) improves cutting action by creating a relief angle as defined by the sloped cutting edges 86. The peripheral cutting edge 84 defines a racetrack shaped opening 90 within the cutting collar 80. As with the embodiment of FIG. 1, the opening formed in the blood vessel wall is also racetrack-shaped.

Figure 13:
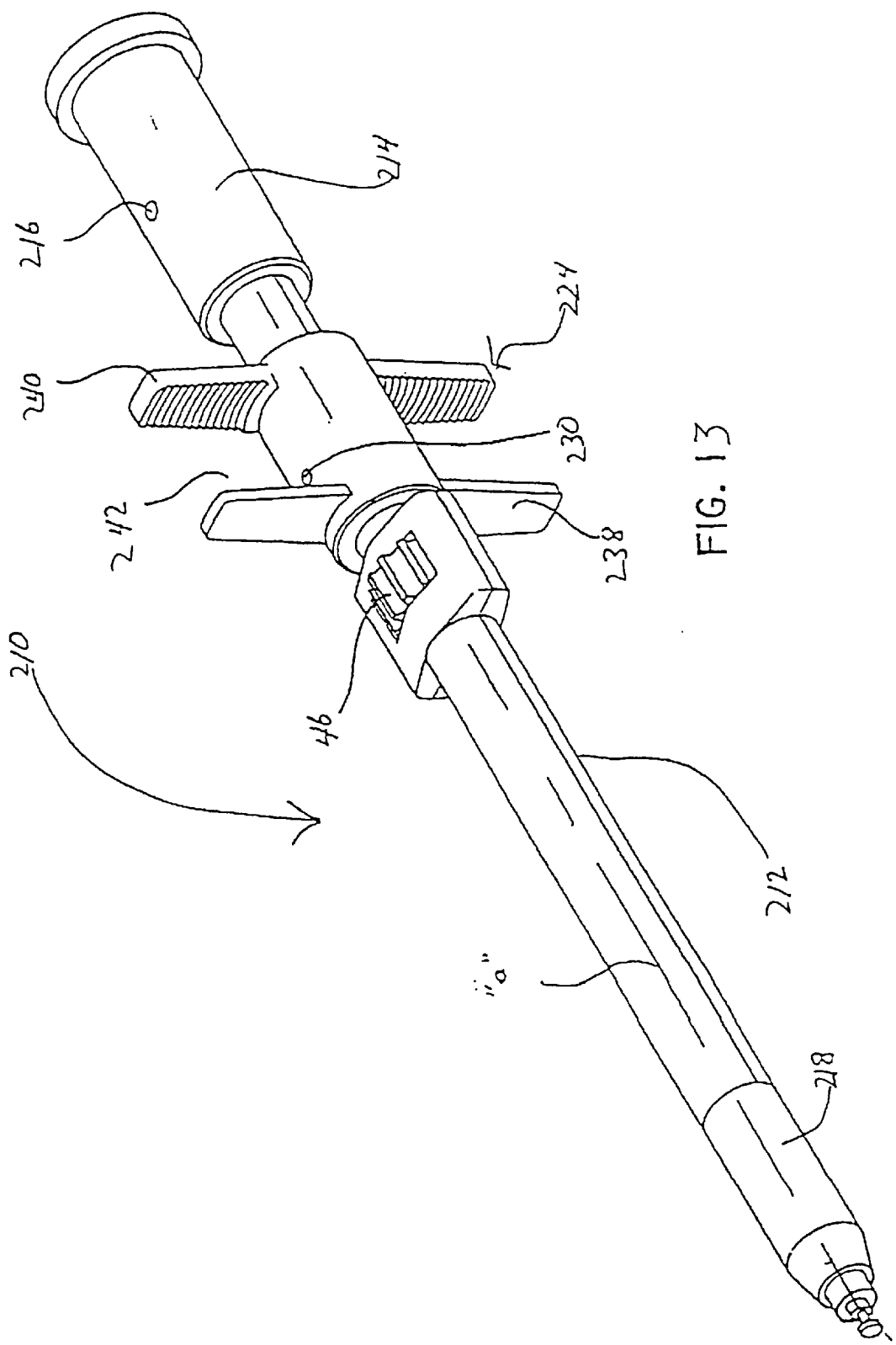
FIG. 13 is a perspective view with parts separated of the apparatus for forming a opening in a wall of a blood vessel in accordance with the principles of the present disclosure.

FIGS. 11 and 12 illustrate an alternate embodiment of the cutting collar and punch head of the apparatus. In accordance with this embodiment, punch head 92 defines head portion 94 having a peripheral cutting edge 96 defining an oblate configuration as shown. Cutting collar 98 also has an oblate peripheral cutting edge 100 defining an oblate-shaped opening 102. The respective cutting edges operate in a similar manner to that described above in connection with the embodiment of FIG. 1 to form an oblate-shaped opening in the blood vessel wall. Referring now to the drawings wherein like reference numerals identify similar structural elements herein, FIG. 13 illustrates in perspective view the apparatus constructed in accordance with a preferred embodiment of the present disclosure and designated generally by reference numeral 210. Surgical apparatus 210 is particularly contemplated for facilitating the formation of an elliptical hole in the aorta during a coronary artery bypass grafting (CABG) procedure. However, other uses for apparatus 210 are also contemplated where it is desirable to form a hole in tissue.

Figure 14:
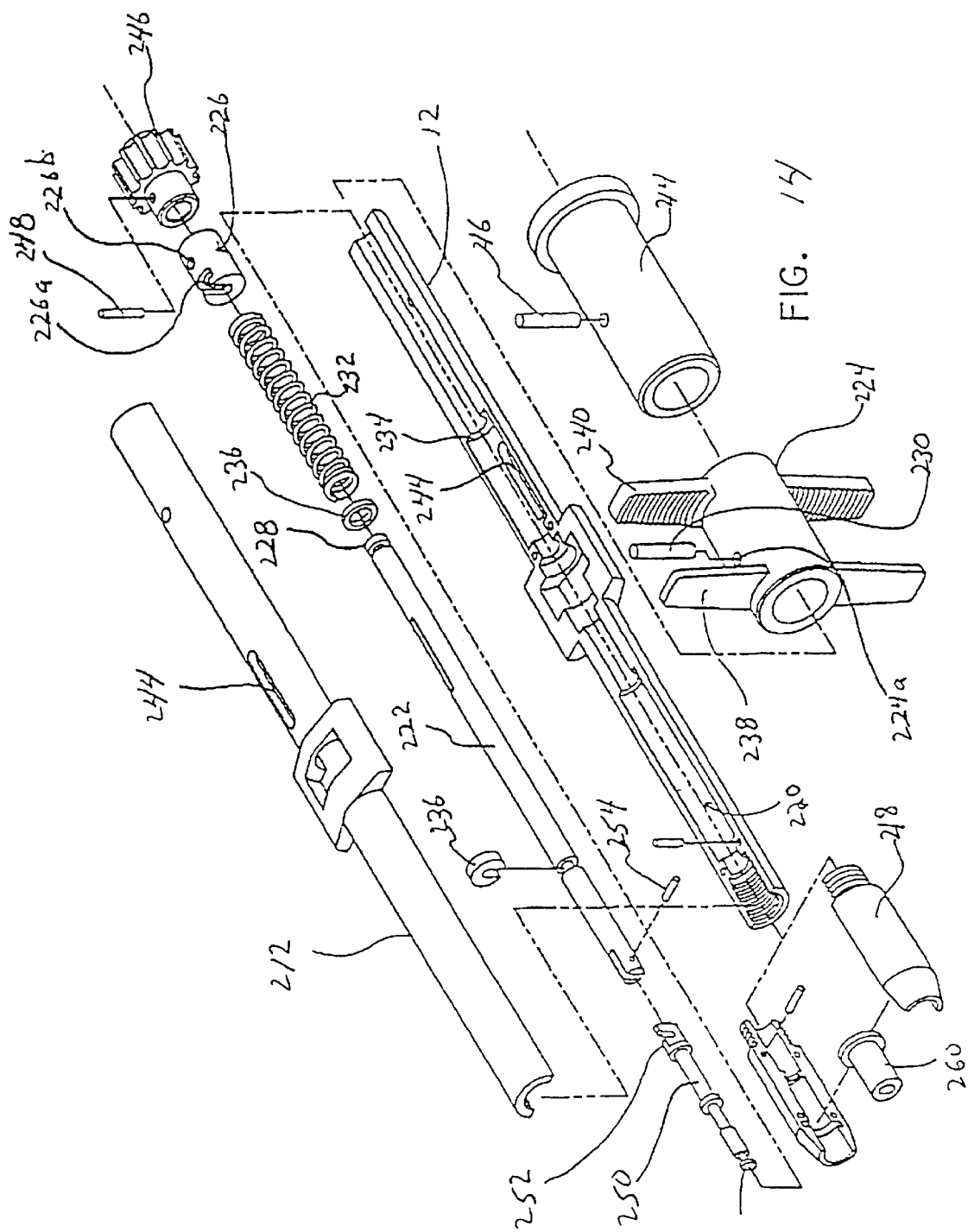
FIG. 14 is a perspective view with parts separated of the apparatus of FIG. 13.
Figure 15:
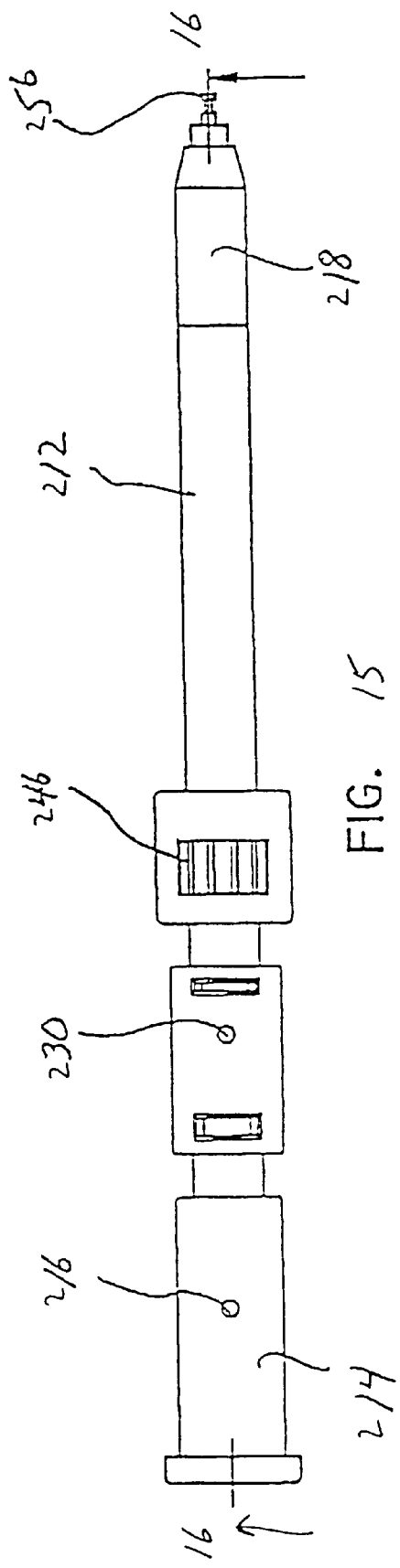
FIG. 15 is a side plan view of the apparatus.

Referring now to FIGS. 13–15, apparatus 210 includes an elongate body 212, handle 214 mounted about the proximal end of the elongate body 212 through mounting pin 216 and nose piece 218 mounted to the distal end of the elongate body 212. Elongate body 212 defines a longitudinal axis "a" and has an opening 220 extending therethrough to define a sleeve-like configuration shown. Elongate body 212 is preferably fabricated from a suitable material such as stainless steel, aluminum or a rigid polymeric material, e.g., polycarbonate.

With reference to FIG. 16, in conjunction with FIGS. 13–15, apparatus 210 further includes an actuating rod 222 extending within the opening 220 of elongate body 212. Actuating rod 222 is adapted for reciprocal longitudinal movement within elongate body 212 as will be discussed. An actuating member 224 is operatively connected to actuating rod 222 to effect reciprocal longitudinal movement of actuating rod 222. In a preferred arrangement, an actuating collar 226 has a U-shaped recess 226a which receives the grooved proximal head portion 228 of actuating rod 222 (FIG. 14). Actuating collar 226 is, in turn, connected to actuating member 224 through actuating pin 230 traversing bores 224a and 226b of actuating member 224 and actuating collar 226, respectively. Other means for connecting actuating member 224 and actuating rod 222 are envisioned as well. Actuating rod 222 is spring biased distally by spring 232 which engages at its proximal end support surface 234 of elongate body 212 and at its distal end spring support collar 236 mounted to the actuating rod 222.

Actuating member 224 includes first and second lever portions 238, 240. Lever portions 238, 240 define a space 242 therebetween which accommodates the fingers of the user during application of the apparatus. Actuating member 224 is capable of moving proximally (to the left in FIG. 16) relative to elongate body 212 and distally while actuating pin 230 travels in diametrically opposed slots 244 defined in elongate body 212.

Apparatus 210 further includes a manually operable rotatable member 246 mounted about elongate body 212. Rotatable member 246 is operatively connected to actuating rod 222 via connecting pin 248. Accordingly, rotation of rotatable member 246 causes actuating rod 222 to rotate, the significance of which will be discussed in greater detail below.

Referring now to FIG. 17, in conjunction with FIGS. 14–16, a punch rod 250 is connected to the distal end of actuating rod 222. In a preferred arrangement, punch rod 250 defines a proximal U-shaped collar portion 252 which is positioned in the grooved distal end of actuating rod 222. A pin 254 traverses corresponding bores in collar portion 252 and punch rod 250 to connect the two components whereby rotational and/or longitudinal movement of actuating rod 222 effects corresponding movement of punch rod 250. With particular reference to FIGS. 17–18, punch rod 250 has distal cutting head 256 which defines proximally facing peripheral cutting edge 258. Distal cutting head 256 defines a generally elliptical configuration as shown.

With reference again to FIG. 17, a cutting collar 260 is mounted adjacent the distal end of nose piece 218. Cutting collar 260 has an axial bore 262 which accommodates at least a portion of punch rod 250. The proximal end of cutting collar 260 defines a flange portion 264 which is received in a corresponding recess 266 defined in nose piece 218 and is capable of rotating within the recess 266. The distal end of cutting collar 260 defines a distal peripheral cutting edge 268 which faces cutting edge 258 of cutting head 256. As best depicted in FIG. 19, the axial bore 262 defines a generally elliptical cross-section corresponding to the cross-sectional dimension of punch rod 250 received within the axial bore 262. Rotation of punch rod 250 as effectuated through rotatable member 246 causes corresponding rotation of cutting collar 260. FIGS. 20–22 illustrate the corresponding rotational movement of punch rod 250, cutting head 256 and cutting collar 260 upon rotation of rotatable member 246 in the direction depicted in FIG. 20.

An alternate embodiment of the distal cutting head configuration of the punch rod is shown in FIG. 18A. The cutting head 258a has flattened sides 257a, 257b. FIG. 19A shows an alternate embodiment of the cutting collar, designated by reference numeral 260a, which has a bore shaped to conform to the cross-sectional configuration of cutting head 258a of FIG. 18A.

Referring now to FIG. 23, by way of example, the use of the apparatus 10 in conjunction with forming an elliptical opening in the wall of a blood vessel, e.g., the aorta, for grafting of a vein during cardiac surgery will be discussed. As depicted in FIG. 23, distal cutting head 256 of punch rod 250 is inserted through an incision provided in the aorta wall "w". Preferably, the wall portion is accommodated within an arcuate recessed portion 270 of punch rod 250. It is to be appreciated that recessed portion 270 assists in retaining the vessel wall portion in a desired position relative to cutting head 256. Thereafter, rotatable member 246 is rotated as desired to cause corresponding rotation of distal cutting head 256 and cutting collar 260 in the manner discussed above and as illustrated in FIGS. 20–22, to properly orient the cutting surfaces of the apparatus. In particular, the rotatable feature permits the surgeon to selectively orient the cutting surfaces of the apparatus, to properly orient the elliptical opening being formed in the blood vessel wall.

Once the cutting surfaces are properly oriented, actuating member 224 is moved proximally to move actuating rod 222 and punch rod 250 proximally as indicated in FIG. 24 against the bias of spring 232. It is to be noted that in FIG. 24, actuation member 224 and actuating rod 222 are fully retracted. With reference to FIG. 25, which shows an intermediate position of actuating rod 222, during proximal movement of cutting head 256, the vessel wall "w" is interposed between cutting edge 258 of the cutting head 256 and cutting edge 268 of cutting collar 260. Further proximal movement of actuating member 224 and distal cutting head 256 causes a shearing action on the blood vessel wall "w" to form the elliptical opening depicted in FIG. 27. Grafting of a vein is then performed as described above.

FIGS. 28–30 illustrate an alternate embodiment of the apparatus of FIG. 1. This apparatus 280 is similar to the apparatus of FIG. 13, but, possesses a different configuration of the actuating member 282. More particularly, actuating member 280 is generally disc shaped and enlarged to accommodate the hand of the user when greater force is required to drive the actuating rod 222. Apparatus 280 further differs from the prior embodiment by eliminating the need for rotatable member 246. It also eliminates the need for actuating collar 226 since, as shown, actuating rod 222 can be directly connected to disc 282 with pin 230. It is envisioned that the surgeon may selectively orient cutting head 256 of punch rod 250 and cutting collar 260 by manipulating disc-shaped actuating member 282 as desired. FIG. 29 depicts apparatus 80 in the unactuated position with cutting head 256 of punch rod 250 displaced from cutting edge 268 of cutting collar 260 to receive the vessel wall. FIG. 30 depicts apparatus 280 in the actuated position with actuating rod 222 and punch rod 250 fully retracted to cut the tissue as effectuated through moving disc-shaped member 282 proximally.

As indicated above, the elliptical hole formed in the blood vessel wall by the apparatus of the present disclosure provides significant advantages. In particular, the elliptical configuration is particularly useful in a grafting procedure when using an anastomosis instrument such as the apparatus disclosed in copending application Ser. No. 08/685,385, filed Jul. 23, 1996, now U.S. Pat. No. 5,707,380. Moreover, the elliptical configuration assists in everting of the blood vessel to appropriately position the vessel walls portions adjacent the opening with respect to the apparatus for firing of the anastomosis clips or staples. In addition, since the vein graft is typically attached to the aorta at an angle less than 90 because its end is cut at an angle, the elliptical configuration better conforms to the shape of the cut end of the graft to facilitate and enhance the anastomosis.

While the above description contains many specifics, these specifics should not be construed as limitations on the scope of the disclosure, but merely as exemplifications of preferred embodiments thereof. It is envisioned that the head portion of each punch head may have blunt edges whereby only the cutting collar possesses the cutting edges. Similarly, the cutting collar may be provided with blunt edges while the punch head has sharp cutting edges. Those skilled in the art will envision many other possible variations that are within the scope and spirit of the disclosure as defined by the claims appended hereto.

What is claimed is:

1. An apparatus for forming a non-circular opening in tissue, which comprises:
    a) an elongate body defining a longitudinal axis and having a proximal end portion and a distal end portion, the distal end portion having a first tissue engaging edge associated therewith;
    b) a punch head disposed adjacent the distal end portion of the elongate body, the punch head defining a second tissue engaging edge associated therewith;
    c) the first and second tissue engaging edges each defining a general racetrack configuration characterized by first and second opposed straight edge portions interconnected by generally arcuate edge portions;
    d) at least one of the first and second tissue engaging edges being adapted to cut tissue; and
    e) the elongate body and the punch head adapted for relative movement such that the first and second tissue engaging edges cooperate to cut tissue disposed therebetween to thereby form a general racetrack-shaped opening in tissue.

2. The apparatus according to claim 1 wherein the first and second tissue engaging edges are each adapted to cut tissue.

3. An apparatus for forming a non-circular opening in the wall of a blood vessel, which comprises:
    a) a housing;
    b) an elongate body mounted with respect to the housing and defining a longitudinal axis, and having proximal and distal end portions;
    c) a cutting element associated with the distal end portion of the elongate body, the cutting element having a peripheral cutting edge defining a longitudinal opening in the cutting element, the peripheral cutting edge defining a general racetrack configuration;
    d) a punch element disposed adjacent the distal end portion of the elongate body and operatively connected to the housing, the punch element having a punch head dimensioned to support tissue; and
    e) at least one of the elongate body and the housing movable relative to the other between an unactuated position wherein the peripheral cutting edge of the cutting element and the punch head of the punch element are displaced and an actuated position wherein the peripheral cutting edge and the punch head are approximated to cooperate to cut tissue supported by the punch head.

4. The apparatus according to claim 3 wherein the peripheral cutting edge of the cutting element has opposed straight edge portions connected by arcuate edge portions.

5. The apparatus according to claim 3 wherein the cutting element defines a general dome-shape to thereby define sloped peripheral cutting edges.

6. The apparatus according to claim 4 wherein the punch head defines a cross-sectional dimension approximating an internal dimension of the longitudinal opening of the cutting element such that in the actuated position the punch head is at least partially received within the longitudinal opening.

7. The apparatus according to claim 6 wherein the punch head defines a peripheral cutting edge adapted to cooperate with the peripheral cutting edge of the cutting element to cut tissue.

8. The apparatus according to claim 7 wherein the peripheral cutting edge of the punch head defines a general racetrack configuration having opposed straight edge portions connected by arcuate edge portions.

9. The apparatus according to claim 3 further including an actuating member operatively connected to the elongate body.

10. The apparatus according to claim 3 further including an elongate member disposed within the elongate body for operatively connecting the housing and the punch head.

11. The apparatus according to claim 3 wherein the punch element includes a recessed portion adjacent the punch head, the recessed portion dimensioned to accommodate tissue portions.

12. The apparatus according to claim 3 including a resilient member for biasing the elongate body to the unactuated position.

13. An apparatus for facilitating the formation of an opening in the wall of a blood vessel, which comprises:
    a) an elongate housing having a proximal end portion and a distal end portion and defining a longitudinal axis;
    b) a cutting collar disposed at the distal end portion of the elongated housing and rotatably mounted thereto, the cutting collar having a longitudinal opening and defining an internal dimension;

c) an actuating rod at least partially disposed in the elongate housing, the actuating rod mounted for longitudinal movement relative to the elongate housing between an unactuated position and an actuated position;

d) a punch blade disposed at the distal end of the actuating rod, the punch blade defining a cross-sectional dimension having a major dimension greater than a minor dimension, the cross-sectional dimension approximating the internal dimension of the cutting collar such that upon movement of the elongate rod to the actuated position the punch blade is at least partially received in the cutting collar to a blood vessel wall disposed therebetween; and e) a manually operable member disposed adjacent the proximal end portion of the elongate housing, the manually operable member operatively connected to the cutting collar and the punch blade and moveable to cause corresponding rotational movement of the cutting collar and the punch blade.

14. The apparatus according to claim 13 wherein the cutting collar has an internal dimension defining an arcuate configuration and wherein the punch blade defines an arcuate cross-sectional dimension approximating the internal dimension of the cutting collar to permit at least partial reception of the punch blade.

15. The apparatus according to claim 13 wherein the cutting collar has an internal dimension defining a general elliptical configuration and wherein the punch blade defines a general elliptical configuration approximating the internal dimension of the cutting collar.

16. The apparatus according to claim 13 further including an actuating member disposed adjacent the proximal end portion of the elongate housing, the actuating member operatively connected to the actuating rod and moveable to cause corresponding movement of the actuating rod between the unactuated position and the actuated position.

17. The apparatus according to claim 13 wherein the actuating rod includes a recessed portion adjacent the punch blade, the recessed portion dimensioned to accommodate at least a portion of the blood vessel wall.

18. The apparatus according to claim 13 wherein the manually operable member is mounted for rotational movement relative to the elongate housing.

19. The apparatus according to claim 18 including a resilient member for biasing the actuating rod to the unactuated position.

20. An apparatus for facilitating the formation of an opening in a wall of a blood vessel, which comprises:

a) an elongate housing having a proximal end portion and a distal end portion and defining a longitudinal axis;

b) a support collar mounted adjacent the distal end portion of the elongate housing and rotatably moveable relative to the elongated housing, the collar having a longitudinal opening and defining an internal dimension;

c) an elongate rod at least partially disposed in the elongate housing, the elongate rod and elongate housing adapted for relative movement;

d) a punch head disposed at a distal end portion of the elongate rod, the punch head defining a cross-sectional dimension having a major dimension greater than a minor dimension, the cross-sectional dimension approximating the internal dimension of the collar such that upon relative movement of the elongate rod and the elongate housing from a first position to a second position, the punch head is at least partially received within the longitudinal opening of the support collar to cut an opening in a blood vessel wall disposed therebetween, at least one of the collar and the punch head having a cutting edge; and e) a manually operable member disposed adjacent the proximal end portion of the elongate housing, the manually operable member operatively connected to the collar and the punch head and moveable to cause corresponding rotational movement of the collar and the punch head.

21. The apparatus according to claim 20 wherein the internal dimension of the collar defines a general elliptical configuration and wherein the punch head defines a general elliptical configuration approximately the internal dimension of the collar.

22. The apparatus according to claim 20 further including an actuating member disposed adjacent the proximal end portion of the elongate housing, the actuating member operatively connected to one of the punch head and the collar, the actuating member moveable to cause the relative movement of the collar and the punch head between the first position and the second position.

23. The apparatus according to claim 21 wherein the collar includes a peripheral cutting edge and wherein the punch head includes a peripheral cutting edge, the peripheral cutting edges cooperating to form the opening in the blood vessel wall.

24. The apparatus according to claim 20 wherein the collar is stationary and the punch head is retractable to form the opening in the blood vessel wall.

25. The apparatus according to claim 23 wherein the elongate rod includes a recessed portion adjacent the punch blade, the recessed portion dimensioned to accommodate at least a portion of the blood vessel wall.

26. A method for forming an opening in a blood vessel wall, comprising the steps of:

a) providing an instrument including an elongate body having a first tissue engaging edge disposed at a distal end thereof, and a tissue supporting head disposed beyond the distal end of the elongate body and defining a second tissue engaging edge, the first and second tissue engaging edges each defining a general racetrack configuration having opposed straight edge portions connected by arcuate edge portions, at least one of the first and second tissue engaging edges being adapted to cut tissue;

b) positioning the tissue supporting head of the instrument through an incision in the blood vessel wall; and c) moving at least one of the elongate body and the tissue supporting head relative to the other to cause the first and second tissue engaging edges to cooperate to cut vessel wall portions supported by the tissue supporting head to thereby form a general racetrack-shaped opening in the blood vessel wall.

27. The method according to claim 26 wherein each of the first and second tissue engaging edges are adapted to cut tissue and wherein the step of moving includes shearing the vessel wall portion through cooperation of the first and second tissue engaging edges.

28. The method according to claim 26 wherein the step of moving includes advancing the elongate body to cause corresponding advancing movement of the first tissue engaging edge to thereby cut the tissue.

29. The method according to claim 26 wherein the step of moving includes retracting the tissue supporting head to cause corresponding retracting movement of the second tissue engaging edge to thereby cut the tissue.

* * * * *